(12) United States Patent
Verbiest et al.

(10) Patent No.: US 6,762,917 B1
(45) Date of Patent: Jul. 13, 2004

(54) METHOD OF MONITORING ESC LEVELS AND PROTECTIVE DEVICES UTILIZING THE METHOD

(75) Inventors: Noel Verbiest, San Jose, CA (US); Lyle Nelsen, San Jose, CA (US); Steven B. Heymann, San Jose, CA (US)

(73) Assignee: Novx Corporation, San Jose, CA (US)

( * ) Notice: Subject to any disclaimer, the term of this patent is extended or adjusted under 35 U.S.C. 154(b) by 216 days.

(21) Appl. No.: 09/880,202

(22) Filed: Jun. 12, 2001

(51) Int. Cl.[7] .................................................. H02H 9/00
(52) U.S. Cl. ........................................... 361/42; 361/56
(58) Field of Search ............................. 361/42, 43, 44, 361/46, 47, 48, 49, 50, 56, 58, 111, 115, 45

(56) References Cited

U.S. PATENT DOCUMENTS

| | | | | |
|---|---|---|---|---|
| 3,784,842 A | * | 1/1974 | Kremer ....................... 307/326 |
| 4,042,967 A | * | 8/1977 | Yamamoto ................... 361/45 |
| 4,080,640 A | * | 3/1978 | Elms et al. ................... 361/45 |
| 4,175,255 A | * | 11/1979 | Linnman et al. ............. 307/326 |
| 4,558,309 A | * | 12/1985 | Antonevich .................. 340/649 |
| 4,710,751 A | * | 12/1987 | Webster ....................... 340/522 |
| 5,051,732 A | * | 9/1991 | Robitaille .................... 340/650 |
| 5,514,964 A | * | 5/1996 | Benesh et al. ............... 324/509 |
| 5,856,902 A | * | 1/1999 | Hashimoto et al. .......... 361/42 |
| 5,946,173 A | * | 8/1999 | Packard et al. .............. 361/42 |
| 6,522,033 B1 | * | 2/2003 | Nevo .......................... 307/125 |

* cited by examiner

*Primary Examiner*—Brian Sircus
*Assistant Examiner*—Danny Nguyen
(74) *Attorney, Agent, or Firm*—The Kline Law Firm

(57) ABSTRACT

A method of controlling and monitoring voltage potential on a human body that includes the following steps: a) Connecting the human body to a "Quasi Virtual Ground"; b) Providing contact with the human skin via one or more silver/silver chloride electrodes; c) Continuously monitoring the triboelectric current i(t) flowing into the "Quasi Virtual Ground" terminal; d) Determining whether or not a person is properly wearing his/her body electrode; e) Including circuitry that immediately interrupts the path-to-ground when a dangerously large current is detected; f) Including circuitry that immediately interrupts the path-to-ground when the power supply to the workstation monitor is interrupted, either intentionally or accidentally.

7 Claims, 9 Drawing Sheets

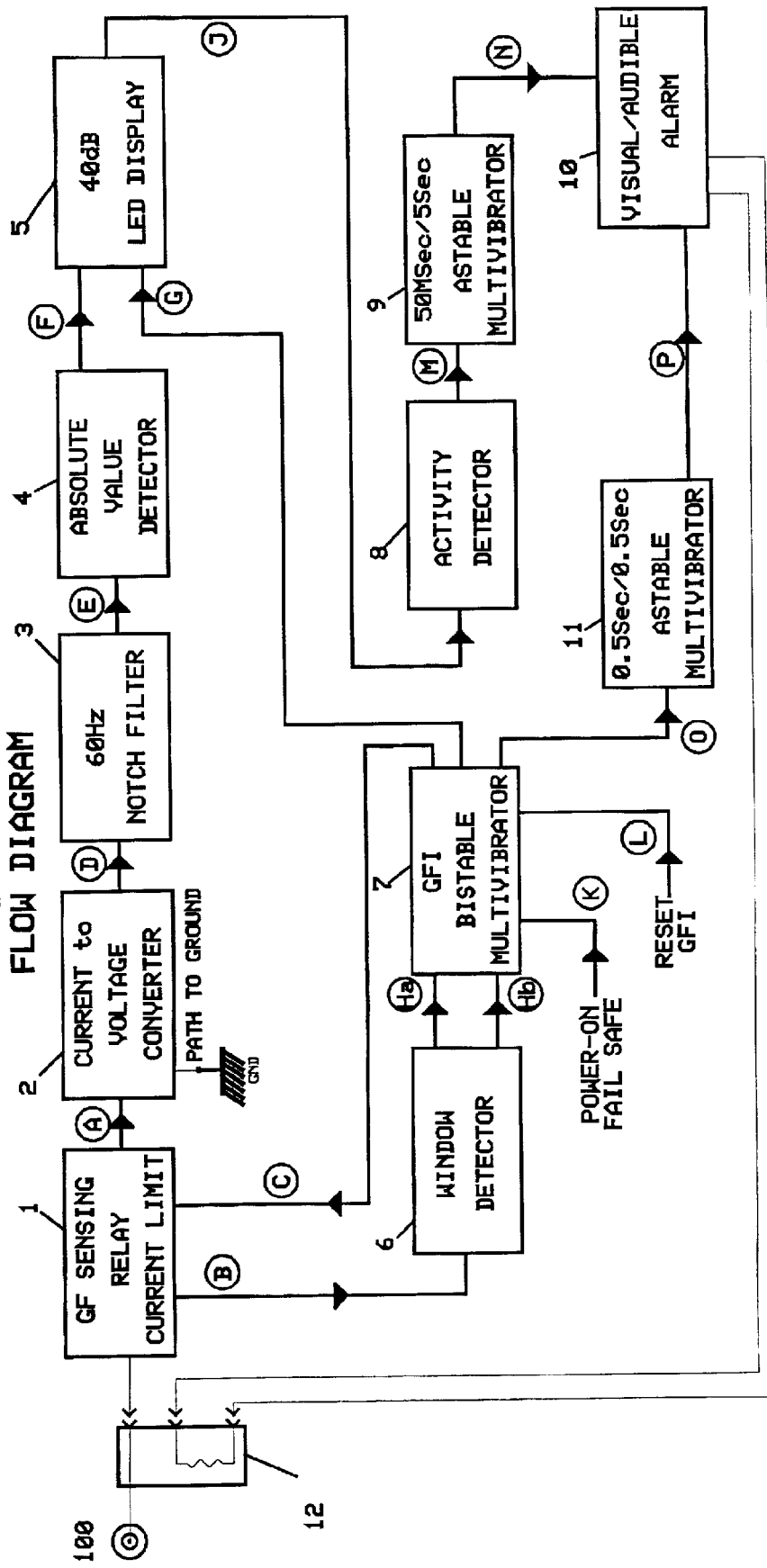

BLOCK DIAGRAM

FIGURE 7
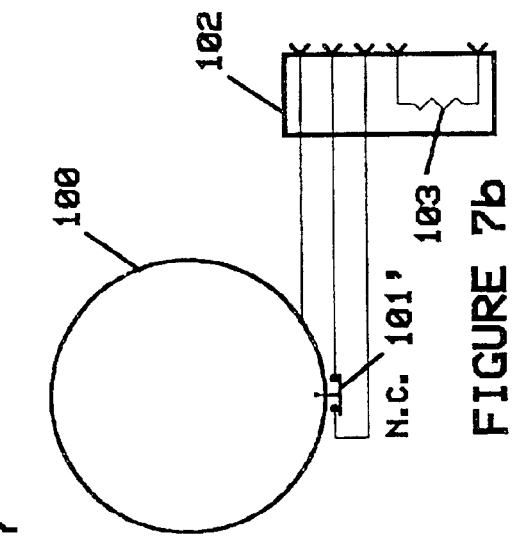
FIGURE 7a
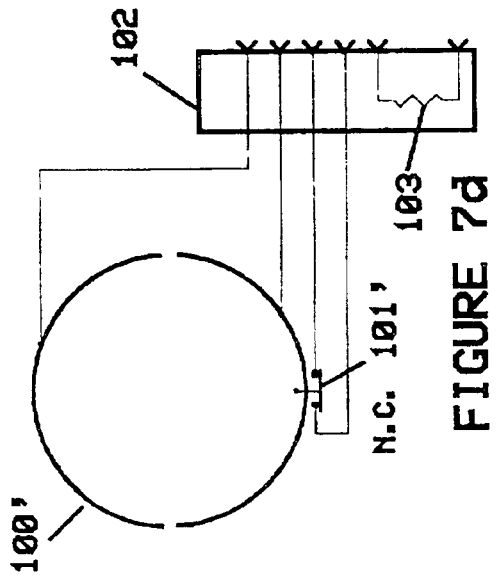
FIGURE 7b
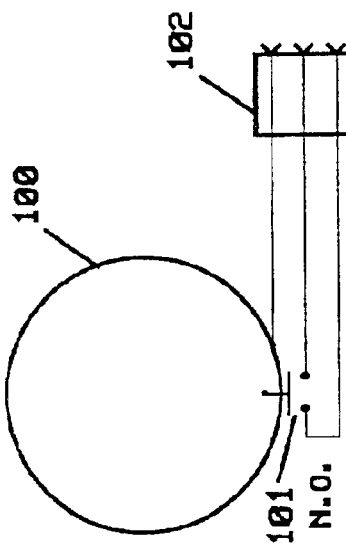
FIGURE 7c
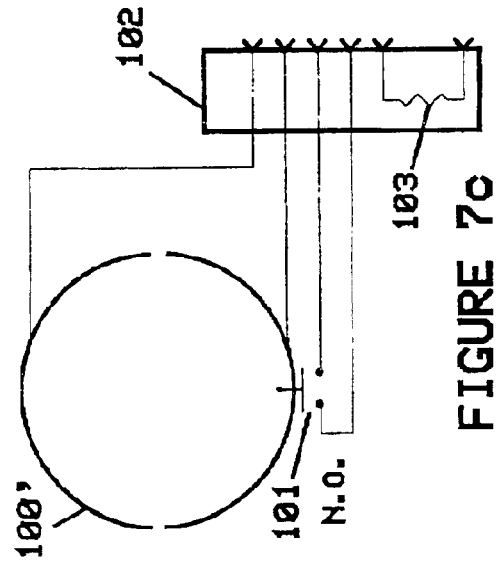
FIGURE 7d

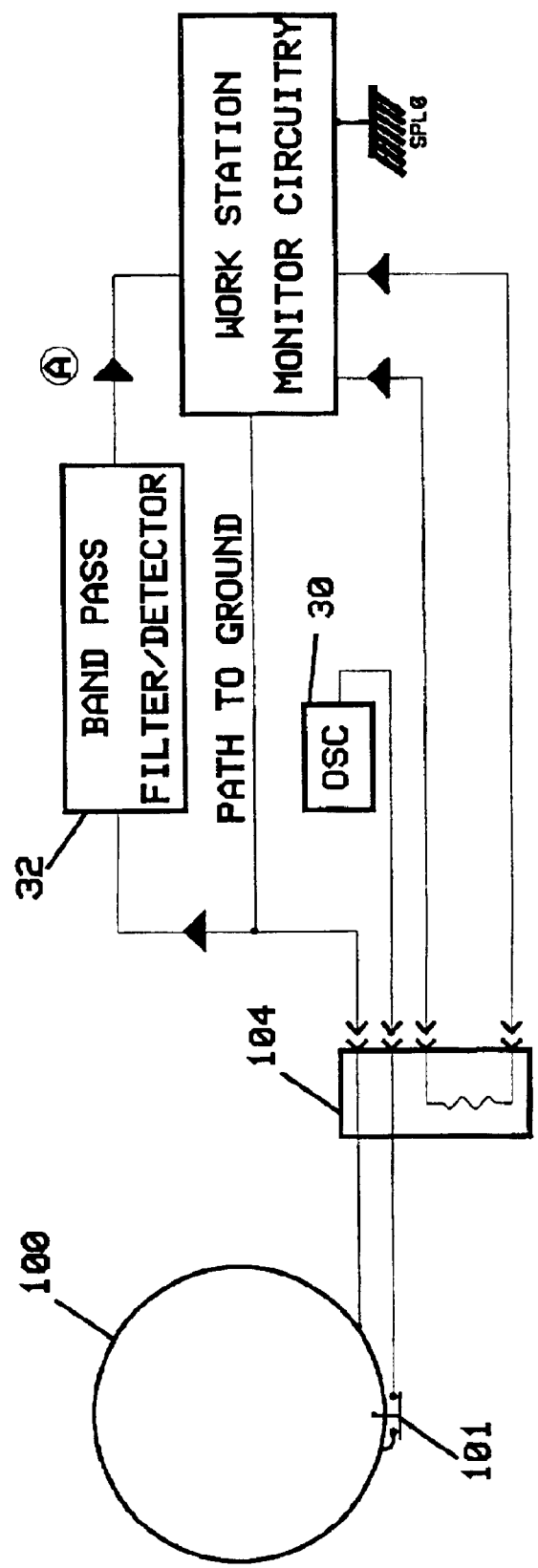

METHOD OF MONITORING ESC LEVELS AND PROTECTIVE DEVICES UTILIZING THE METHOD

FIELD OF THE INVENTION

The present invention relates generally to ESC monitoring devices and ESC protective devices, and more particularly is a method of monitoring tribolelectric current generated in an operator's body, and thereby controlling ESC levels on the operator's body.

BACKGROUND OF THE INVENTION

The present invention is based on the underlying mechanisms which cause electrostatic potentials to build up on human or other bodies. These mechanisms are used to provide improved and simplified methods for elimination of electrostatic potentials. The present invention also addresses the voltage potentials which are capacitively coupled into human or other bodies by power distribution wiring or by other naturally occurring or man-made electric fields.

The build up of electrostatic potentials on the human body when a person walks over a carpeted surface and when that person subsequently feels the unpleasant discharge when touching a door-knob has been experienced by countless numbers of people. Likewise, existence of capacitively coupled low frequency potentials, mostly from power distribution wiring, can be relatively easily demonstrated by touching an input of an audio amplifier with a finger, which results in a loud hum emanating from the speakers.

The capacitively coupled voltage potentials from power distribution wiring have been traditionally largely ignored because their peak amplitudes are relatively small in comparison with the ones from electrostatic origin. In practice, when measuring these potentials, one finds peak amplitudes well below one kilovolt, whereas peak amplitudes from triboelectric charging are easily an order of magnitude higher. The neglect is further compounded by the fact that a human body discharge below 3 kilovolts is usually not physically felt. However, state of the art electronic devices and micro-structures have become so electrostatic discharge sensitive that one can no longer neglect the effects of low voltage potential discharges such as the ones from capacitively coupled low power line electric fields. All further references to human body voltage potentials in the application therefore imply potentials of triboelectric origin as well as potentials resulting from capacitively coupled electric fields.

In order to reduce and eliminate the detrimental effects of voltage potential discharges from human bodies, a number of devices have been developed. The most common of these devices is the "grounded wrist strap". The grounded wrist strap is basically a wrist-worn bracelet made of a conductive material. The bracelet makes electrical contact with a person's skin, and is connected to protective earth or other electrical common reference plane (subsequently referred to as the "ground") via a lead wire. Usually a resistor with a value of at least one megaohm is inserted in this path-to-ground. The choice of the resistance value is a compromise between the need to adequately bleed-off the voltage potential charges, and, the need to avoid electric shock and/or electrocution when a person wearing such a grounded bracelet accidentally touches a live power distribution wire.

However, as shall be demonstrated below, the 1 Mohm or higher resistor does not reduce the voltage potentials sufficiently close to zero, and does thus not provide adequate protection during handling of state of the art electronic structures and devices. Under certain circumstances, instantaneous peak voltages of tens to hundreds of volts can be measured in spite of such grounding. State of the art Magneto Resistive (GMR, TMR, etc. . . . ) magnetic disk drive heads and sub-micron semiconductor structures can be destroyed with a human body voltage discharge of as low as 5 volts.

In addition to the wrist straps, it is also common industry practice to use "Workstation Monitors" in conjunction with the wrist straps. The purpose of the workstation monitors is at least twofold: (1) to establish a controlled path-to-ground, and, (2) to verify whether or not a wrist strap is being properly worn. Verification of whether or not a wrist strap is being properly worn is usually accomplished by dividing the wrist strap into two sections isolated from each other. In a typical detection approach, a small measuring current is sent through the wearer's skin between the isolated sections. By measuring the voltage drop across the isolated sections, a decision can be made whether the user's wrist is present or not. If a wrist is indeed present, it is further assumed that a proper connection to ground most likely exists.

The disadvantages of existing wrist straps, whether the split or the non-split version, in conjunction with their existing workstation monitors, are as follows:

1. The 1 Mohm or higher resistor in the path-to-ground allows for body voltage potential excursions well beyond the safe limits of state of the art electronic structures and devices.

2. The value of the resistor in the path-to-ground cannot be lowered due to safety considerations.

3. None of the existing wrist strap/workstation monitor combinations determine with scientific certainty whether a true path from wrist to ground actually exists. All known approaches rely on the assumption that the hardware components used in this path seldom fail, and, therefore, the path is assumed to be of high integrity.

4. The interface between commonly used wrist strap materials and the human skin is not optimum. Well understood bioelectric effects cause variability in the contact resistance. Bioelectric potentials, because of the ionic nature of the skin/wrist strap interface, do interfere with the small measurement currents used in the split wrist strap approaches. As will be demonstrated later, it is unlikely that existing wrist straps will ever allow reliable and repeatable paths-to-ground of sufficiently low resistance, so as to meet the necessary 5 volt and lower sensitivities.

5. Certain split wrist strap measurement circuits in existing workstation monitors apply voltages above 5 volts to the wrist-under-test, thus charging the body capacitance to these levels, hence possibly contributing to device destruction rather then to their protection.

The present invention intends to improve on or eliminate all these constraints and limitations. The present invention establishes a method of monitoring and controlling electrostatic charge on a human body. The method utilizes the discovery that the first order phenomenon in the charging of a human body to a voltage potential is in fact an electrical current, and that this current is driven from a near perfect current source of atomic nature. Proof of existence of this triboelectric current can be easily reproduced and demonstrated by connecting a human-under-test to a Current Amplifier, such as the Keithly 428 or equivalent, or, to a simple homemade current-to-voltage operational amplifier circuit with a 1 microamp per volt conversion gain. The output of the amplifier can be observed with a suitable recorder or oscilloscope while the human-under-test walks over a typical electrifying floor surface. In order to eliminate interference from often overwhelming capacitively coupled stray electric fields, the test is best done in a shielded room. Peak triboelectric currents generated by typical shoe sole/floor surface interactions were found to be as high as tens of microamperes. However, the vast majority, estimated at better then 95%, do not exceed 10 microamperes.

The voltage potential which develops on a human body, and which is measurable with any suitable electrometer or electrostatic voltmeter, is thus a direct result of a triboelectric current charging the body capacitance to an instantaneous voltage according to the general equation $dv=(i*dt)/C$. The typical body capacitance is 100 to 150 picofarads, and depends on the size, shape and posture of the body. In fact, the body voltage potential will continuously vary because of the continuous body shape or posture variations, all of which will change the body capacitance. This variation of body voltage potential is a secondary order effect in accordance with the law of conservation of charge ($C1*V1=C2*V2=Q$) which only can take place after the body capacitance was initially charged with a triboelectric current.

For purposes of electrical circuit analysis, the charging phenomenon can be modelled with an equivalent circuit comprising the triboelectric current source $i(t)$, the body capacitance C, and the resistive path-to-ground R is shown in FIG. 1. R represents the parallel circuit of all intentional (such as the 1 Mohm or higher bleeder resistor) and unintentional (such as conductive and ionic leakage paths) resistive paths between the body and ground. From a circuit analysis or spice simulation perspective, it is a first-order circuit driven by a non-constant current source. The source is non-constant because the interactions between the shoe sole and the floor surface are erratic and unpredictable. The total response of this circuit, which yields the instantaneous body voltage potential $v(t)$, invariably starts off with a part which is "transient" in nature (a person starting to walk, for example, or having occasional and infrequent shoe-to-surface interactions for example) and may even out to a "steady state" type response when, for example, a person walks at a steady and regular pace for some distance. Mathematical circuit analysis and/or Spice simulation will show that the peak amplitude of $v(t)$ under the "transient" regime can be significantly higher than the one found under the "steady state" regime. This can be easily verified experimentally by measuring the body voltage potentials with a suitable electrometer or electrostatic voltmeter. The peak voltages measured during a person's initial steps will be considerably higher than the ones measured during the balance of the walk. By the same token, and operator sitting at a workstation, and shuffling his/her feet occasionally and infrequently will produce considerably higher body voltage excursions that the same operator shuffling his/her feet continuously.

A typical current waveform associated with a single step with a nonconductive shoe on a non-conductive carpeted surface is shown in FIG. 2. The waveform can be broken down into four distinct segments: A) heel up, B) ball of the foot up, C) heel down, and, D) ball of the foot down. While the wave shape will generally approximate that shown in FIG. 2, the polarity of the waveform will depend on the specific materials present in a given shoe-to-surface interaction. The same shoe tracked in FIG. 2 would produce a waveform with reversed polarity if the floor surface is different, for instance a hardwood laminate.

When a person is grounded through a resistor, as in existing wrist strap protective devices, triboelectric current $i(t)$ is forced through the parallel circuit formed by the grounding resistor R and body capacitance C. The waveform and the peak amplitude of the resulting voltage ($v(t)$) across the parallel circuit can be determined via mathematical and/or experimental methods. The peak amplitude will be proportional to both the peak amplitude of $i(t)$ and the speed with which $i(t)$ varies over time ($di/dt$). Experimentally, it has been determined that peak current amplitudes of tens of microamps and rates of rise as high as 5 milliamps/sec are not uncommon. When a current transient of this nature is forced to flow through a parallel combination comprising a 1 Mohm grounding resistor and a 100 picofarad body capacitance, a peak voltage potential $v(t)$ of tens of volts will result Similarly, if the resistance in the path-to-ground is 10 Mohm, as in certain existing wrist strap and workstation monitor combinations, a peak body voltage potential of over one hundred volts will result. In both cases, these amplitudes are clearly beyond the survival limits of state of the art electronic structures and devices.

As mentioned above, it was determined experimentally that the majority of shoe-to-floor-surface interactions produce triboelectric peak currents not exceeding 10 microamperes, with rise times not exceeding 2.5 milliamps/second. From this basis, one can determine via mathematical and/or experimental methods, that for a given body capacitance of 100 picofarads, one can limit the peak body voltage excursions to 1 volt if the resistor value in the path-to-ground does not exceed 100 kiloohm. For all practical purposes, with path-to-ground resistances below a few hundred kiloohm, one can approximate the peak body voltage excursion by simple multiplication of the peak current times the path-to-ground resistance. The error made by omitting the effect of the body capacitance is minimal. The 100 kiloohm resistor value of course includes the contact resistance between the wrist strap and the skin of its wearer. As mentioned above, the resistance of current art wrist straps is highly erratic and unpredictable. In fact, values of hundreds of kiloohms on persons with dry skin, particularly when compounded by motion artifact, are quite common. It is thus highly unlikely that the existing wrist straps in combination with their existing workstation monitors will allow for the safe handling of very sensitive state-of-the-art electronic devices and structures which have damage thresholds of 5 volts or less.

Accordingly, it is an object of the present invention to provide a protection/monitoring system that limits potential body voltage excursions within the safe limits of state of the art electronic structures and devices.

It is a further object of the present invention to provide a methodology that allows the resistance in the path-to-ground to be safely lowered.

It is a still further object of the present invention to provide a means to determine with scientific certainty whether a true path from wrist to ground actually exists.

It is another object of the present invention to provide an improved interface between wrist strap materials and the human skin.

It is still another object of the present invention to reduce or eliminate voltages applied to the wrist-under-test, thereby reducing the body voltage potential.

SUMMARY OF THE INVENTION

The present invention is a method of monitoring ESC on a human body comprising the following steps:

a) Connecting the human body to a "Quasi Virtual Ground". The maximum resistance in the path-to-ground does not exceed 10 Kohm, thus insuring that the majority of peak body voltage potential excursions will not exceed 100 millivolts. For all practical purposes, it comes down to the triboelectric current being shunted directly to ground.

b) Providing contact with the human skin via one or more electrodes. The preferred type of electrode is a silver/silver chloride electrode. The chemical, mechanical and electrical properties of silver/silver-chloride electrodes in contact with human skin have been studied extensively by the medical industry and are thus well optimized and understood. With the addition of an adequate gel between the electrodes and the skin, the contact resistance is typically below 2 Kohm, and, the resistance is stable over reasonable amounts of time (days), and is virtually not prone to motion artifact. The silver/silver chloride electrodes could be part of a designed for the purpose bracelet, or they could be pre-gelled disposable adhesive patches similar to the ones used for medical electrocardiography (Holter electrodes). Whatever the means of making contact with the skin, it is very important for the contact resistance to be as low as practical. As a fall back method, one can also use industry standard wrist straps, either the split or the non-split versions, with the herein described workstation monitor, but because of their inherent high and unstable skin contact resistance, body voltage potential excursions exceeding the 5 volt threshold limit are to be expected. Application of a topical conduction improving gel on the wrist could alleviate some of the problems. For the sake of simplification, the means of contact with the skin will be further referred to as the "body electrode".

c) Continuously monitoring the triboelectric current i(t) flowing into the "Quasi Virtual Ground" terminal. The amplitude and polarity of the triboelectric current can be made visible on any suitable visual display device such as, for example, a recorder, an oscilloscope, or a bar graph display with a linear, logarithmic, or custom scale.

d) Determining whether or not a person is properly wearing his/her body electrode and whether or not a true path from wrist to ground actually exists. This determination can be accomplished through a number of methods, none of them requiring a measuring current to be sent through a split body electrode. The methods will be described in detail below.

e) Including circuitry that immediately interrupts the path-to-ground when a dangerously large current is detected. In the present arrangement, with the path-to-ground being of relatively low resistive value, a danger for electroshock and/or electrocution exists in case of accidental contact with a live power distribution wire. Circuitry is therefore included in this novel workstation monitor which will detect and interrupt the path-to-ground nearly instantaneously. A suitable type of visual and audible alarm will be activated concurrently. Deliberate manual reset will be required in order to reestablish the path-to-ground.

f) Including circuitry that immediately interrupts the path-to-ground when the power supply to the workstation monitor is interrupted, either intentionally or accidentally. The path-to-ground will remain open until the deliberate manual reset has been executed.

An advantage of the present invention is that it limits potential body voltage excursions within the safe limits of state of the art electronic structures and devices.

Another advantage of the present invention is that it provides a means to determine with scientific certainty whether a true path from wrist to ground actually exists.

These and other objects and advantages of the present invention will become apparent to those skilled in the art in view of the description of the best presently known mode of carrying out the invention as described herein and as illustrated in the drawings.

BRIEF DESCRIPTION OF THE DRAWINGS

FIG. 3 shows a block diagram of one embodiment of the workstation monitor according to the present invention.

FIG. 7 depicts possible arrangements of bracelet type body electrodes with a switch incorporated in the bracelet.

FIG. 7*a* is a non-split bracelet with a "normally open" switch.

FIG. 7*b* depicts a non-split bracelet with a "normally closed" switch.

FIG. 7*c* is a split bracelet with a "normally open" switch.

FIG. 7*b* depicts a split bracelet with a "normally closed" switch.

FIG. 8 shows a workstation monitor detection scheme utilizing a shared conductor.

DETAILED DESCRIPTION OF THE INVENTION

Figure 2:
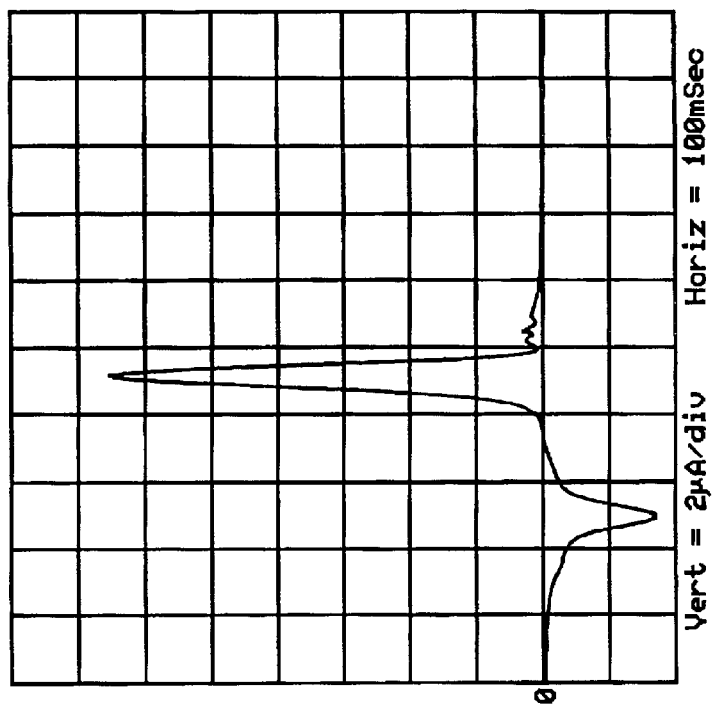
FIG. 2 shows a typical triboelectric current waveform associated with a single step of a person wearing a nonconductive shoe on a non-conductive carpeted surface.
Figure 1:
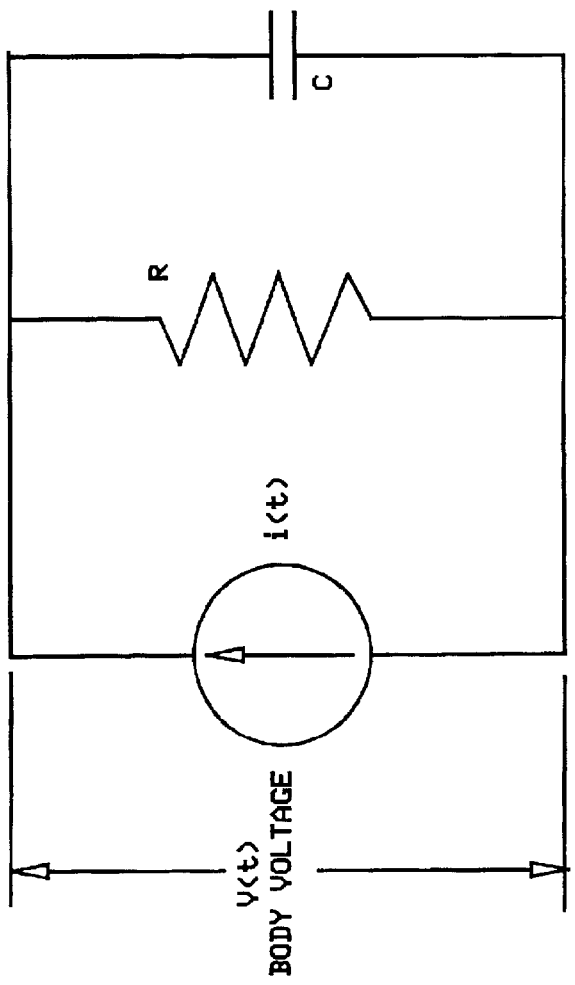
FIG. 1 is a circuit diagram showing the triboelectric current source i(t), the body capacitance C, and the resistive path-to-ground R.

The present invention is a method of controlling and monitoring the voltage potential on a human body comprising the following steps:

a) Connecting the human body to a "Quasi Virtual Ground". The maximum resistance in the path-to-ground does not exceed 10 Kohm, thus insuring that the majority of peak body voltage potential excursions will not exceed 100 millivolts. For all practical purposes, it comes down to the triboelectric or other currents being shunted directly to ground.

b) Providing contact with the human skin via one or more electrodes, preferably silver/silver chloride electrodes. The chemical, mechanical and electrical properties of silver/silver-chloride electrodes in contact with human skin have been studied extensively by the medical industry and are thus well optimized and understood. With the addition of an adequate gel between the electrodes and the skin, the contact resistance is typically below 2 Kohm, and, the resistance is stable over reasonable amounts of time (days), and is not prone to motion artifact. The silver/silver chloride electrodes could be part of a designed for the purpose bracelet, or they could be pre-gelled disposable adhesive patches similar to the ones used for medical electrocardiography (Holter electrodes). Whatever the means of making contact with the skin, it is very important for the contact resistance to be as low as practical. As a fall back method, one can also use industry standard wrist straps, either the split or the non-split versions, with the here described workstation monitor, but, because of their inherent high and unstable contact resistance, body voltage potential excursions exceeding safe levels are to be expected. Application of a topical conduction improving gel on the wrist could alleviate some of the problems. For the sake of simplification, the means of contact with the skin will be further referred to as the "body electrode".

c) Continuously monitoring the triboelectric current i(t) flowing into the "Quasi Virtual Ground" terminal. The amplitude and polarity of the triboelectric current can be made visible on any suitable visual display device such as, for example, a recorder, an oscilloscope, a bar graph display with a linear, logarithmic, or custom scale, or any other suitable display.

d) Determining whether or not a person is properly wearing his/her body electrode. This determination can be accomplished through a number of methods, none of them requiring a measuring current to be sent through a split body electrode. The methods will be described in detail below.

e) Including circuitry that immediately interrupts the path-to-ground when a dangerously large current is detected. In the present arrangement, with the path-to-ground being of relatively low resistive value, a danger for electroshock and/or electrocution exists in case of accidental contact with a live power distribution wire. Circuitry is therefore included in this novel workstation monitor which will detect and interrupt the path-to-ground instantaneously. A suitable type of visual and audible alarm will be activated concurrently. Deliberate manual reset will be required in order to reestablish the path-to-ground.

f) Including circuitry that immediately interrupts the path-to-ground when the power supply to the workstation monitor is interrupted, either intentionally or accidentally. The path-to-ground will remain open until the deliberate manual reset has been executed.

Detection Means:

In the present invention, a number of techniques may be used to provide a means for detection of whether a person is properly grounded or not. These techniques are not mutually exclusive. They can be used in various combinations so as to enhance the overall reliability of the detection method.

Detection of whether or not a bracelet type body electrode is correctly present on a wrist can be made by including an electromechanical switch in the bracelet itself. If sufficient pressure is present on the lever mechanism actuating the switch, contact closure, or opening, will result. A lead wire containing at least two conductors, a first lead wire to establish the path-to-ground, and a second lead wire for detection of the switch closure (or opening) is used between the bracelet and the workstation monitor. The circuitry for this arrangement is described in detail in the Circuit Description section following below.

Another method of detection in the present invention is based on observing the presence or absence of bursts of triboelectric current flow over a certain period of time. In most practical situations, there will be continuous bursts because of an operator's minute involuntary shoe sole/floor surface interactions. If no current flow is detected for a certain period of time, ten seconds for example, an attention drawing visual/audible alarm will be activated. A lack of current flow implies that either the operator is no longer properly connected to the workstation monitor, or that he or she happened to be sufficiently motionless so as to not produce triboelectric current bursts of a certain minimal amplitude during this time period. In the latter case, a minor shuffling of the shoes will produce sufficient current to deactivate the alarm. A lead with a single conductor connects the electrode to the workstation monitor. The alarm can be deactivated by unplugging this lead. A suitable detection mechanism, such as a keyed-for-the-purpose lead connector at the workstation monitor, would serve this purpose. Details of controlling circuitry layouts for this means of detection are given in the Circuit Description section following below.

Still another method of detection is based on the use of split body electrodes such as two disposable patches, electrically isolated from each other, or a split version bracelet. Both body electrodes are connected individually, and are part of two identical virtual ground paths inside the workstation monitor. When worn properly, both paths-to-ground will have similar resistances, and half of the triboelectric current will thus flow down each path. If this is not the case, for example, if one of the paths is open or the contact with the skin has deteriorated, then the current distribution will no longer be equal. Controlling circuitry, described below in the Circuit Description section, can easily detect this situation, and activate an appropriate alarm to draw the operator's attention.

Yet another method of detection is also based on the use of split body electrodes. In this case, one of the electrodes serves to establish the path-to-ground for the triboelectric current, whereas the second electrode is used to measure the body voltage potential. If, for whatever reason, the path-to-ground resistance in the first electrode circuit increases beyond a set limit, the body voltage potential excursion will become unacceptably high. The electrode of the second circuit, connected to a voltmeter type circuit with adequately high input impedance, will detect these voltage excursions, and activate an alarm.

Circuit Description:

FIG. 3 shows a block diagram of one implementation of the novel workstation monitor of the present invention. A single wire lead connects a body electrode 100 such as a single disposable patch electrode or a non-split wrist strap to the workstation monitor. If a patch electrode is used, its location on the body is not critical, and can be selected so as to minimize the interference of the lead wire with the operator's activity. This freedom in attachment of patch electrodes is a distinct advantage over wrist strap type devices which, by design, can only be worn on a wrist. Experience has shown that the level of interference with tools and equipment on a work surface created by a lead connected at the shoulder of an operator, for example, is far less intrusive than a lead attached at the wrist. Excluding the resistance of the copper wire itself, there are no added resistors in the lead connecting the skin contact electrode to the workstation monitor. A suitable keyed connector 12 at the workstation monitor allows for detection of whether or not the lead is plugged in. The key can be electrical, mechanical, or a combination of the two. FIG. 3 depicts an electrical key with a resistor of a certain value. Different values of the resistor can be assigned to identify different models of body electrodes. If the keyed connector 12 is not plugged in, the alarm will be disabled. Detection of a properly worn body electrode is accomplished by the earlier mentioned method of observing the existence of occasional bursts of triboelectric current which are typically associated with shoe sole/floor surface interactions of an operator.

The process begins with the triboelectric current entering the ground fault sensing/relay/current limit stage 1. That signal is then processed through a current-to-voltage converter 2, through a 50/60 Hz notch filter 3, and then through an absolute value amplifier 4. The purpose of the absolute value amplifier 4 is to convert bipolar signals at its input into positive unipolar signals at its output. The unipolar output drives a display 5. In the preferred embodiment, the display 5 is a logarithmic bar graph with a 40 dB span. The bar graph of the preferred embodiment comprises 11 LED's spaced 4 dB's apart. The least significant LED will correspond to 0.1 $\mu A$ of triboelectric current, and the most significant LED will correspond to 10 $\mu A$ Many other executions of the display 5 are suitable for use in the present invention, and are known to those skilled in the art.

From the LED bar graph display 5, a signal J is picked off to drive activity detector stage 8. The activity of the least significant LED is monitored by activity detector 8. If this LED stayed off for more that ten seconds, meaning there was no triboelectric current activity for ten seconds, the activity detector 8 would time out, and send a command to 50 mS/5S astable multivibrator stage 9. Activity detector stage 8 comprises a retriggerable monostable multivibrator. Concurrently with this processing, a signal B is picked off at the ground fault sensing stage 1, and goes to the window detector 6, and from there to the ground fault bistable multivibrator 7 (Ha and Hb). If a positive or negative current would flow in the path-to-ground, exceeding the threshold limits set in window detector stage 6, signals Ha and Hb will activate the ground fault bistable multivibrator stage 7 immediately, which in turn, will cause relay contact in the ground fault sensing/relay/current limit stage 1 to open instantly, thus interrupting the path-to-ground. Both the activity detector stage 8, which detects the presence of triboelectric current bursts, and the ground fault bistable multivibrator 7 have output signals M and 0 which drive 50 mS/5S astable multivibrator 9 and 0.5S/0.5 sec astable multivibrator 11 respectively. Multivibrators 9 and 11 drive a visual/audible alarm 10. In this particular embodiment, a visual/audible 50 mS beep will repeat every five seconds to indicate a lack of triboelectric current bursts, and will beep continuously, (0.5 sec on, 0.5 sec off), if an accidental contact with a live power distribution wire occurs.

Figure 4:
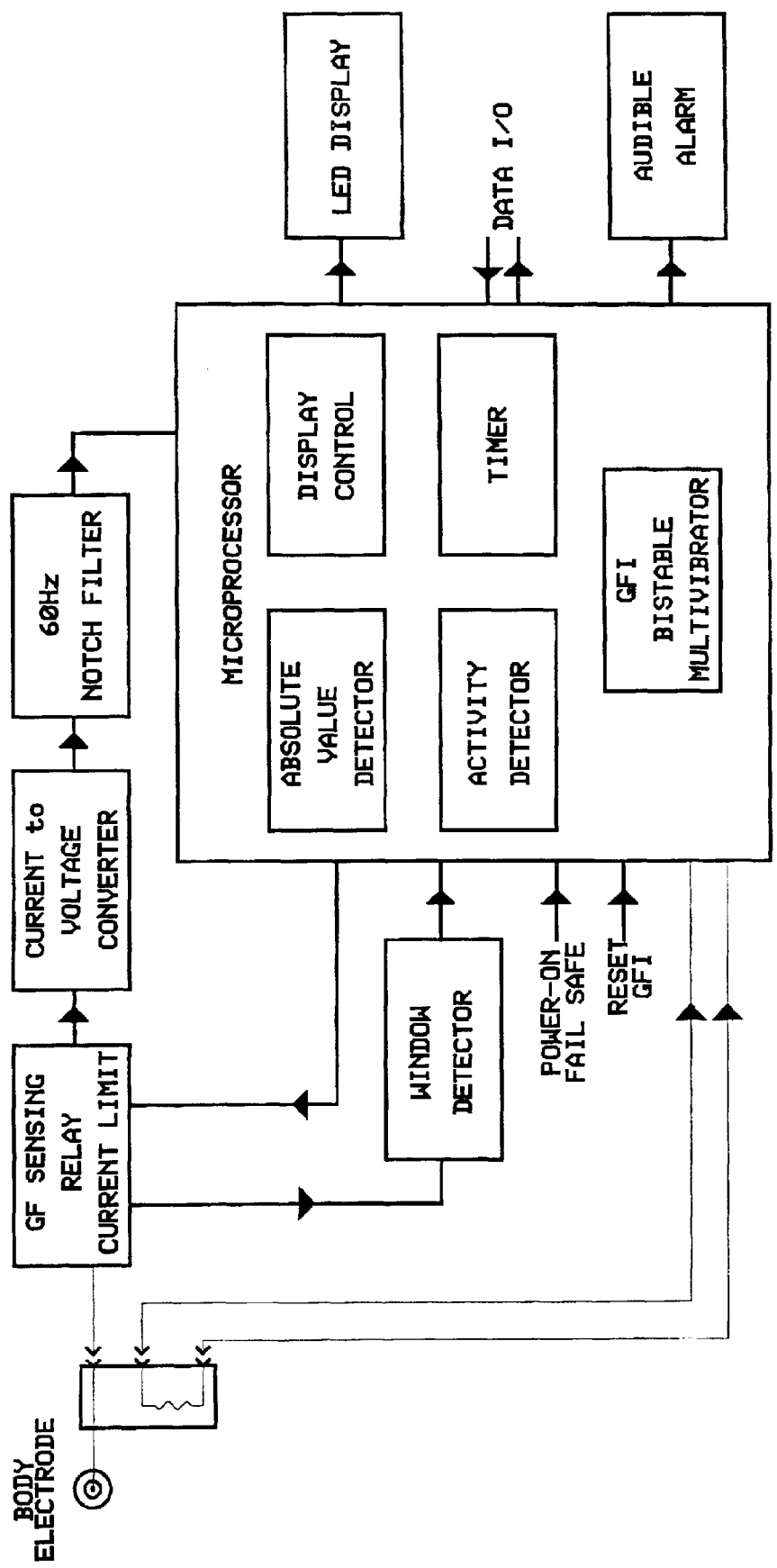
FIG. 4 is a block diagram of a workstation monitor with certain stages executed with a microprocessor.

Ground fault bistable multivibrator 7 output signal C will cause a relay to open in stage 1 if an operator were to accidentally touch a live power wire. Ground fault bistable multivibrator stage 7 output signal G ensures blanking of all the LED's of the bar graph in display stage 5 as long as stage 7 has not been reset manually by signal L (GFI reset). Signal K (power-on fail safe) insures that the bistable multivibrator in stage 7 is set to the proper logical state when an intentional or unintentional power interruption has occurred. At power-up, the relay in stage 1 will always come up in the open (fail safe) state. Assertion of the reset GFI input L is required in order to resume service. Not shown in FIG. 3 are the power supply circuits for the various stages and circuits. It will be obvious to those skilled in the art that this workstation monitor will incorporate power supply circuits. Power is derived form the facilities' regular AC power distribution. It is down-converted and rectified to voltage levels compatible with standard electronic circuits. The power line cord of the workstation monitor includes the standard three wires, one of them being the ground wire (the "green wire"). The path-to-ground for the triboelectric current includes this green wire. The current cannot flow, that is, there is no current, if the green wire is not present, or if for some reason, the green wire is not connected to earth, either by accident or by an intentional act. This will result in an alarm situation, identical to the one described earlier under the lack of triboelectric bursts. FIG. 4 shows a block diagram of a workstation monitor with equivalent functionality to that shown in FIG. 3, but in which certain of the stages are executed with a microprocessor. In the scheme illustrated in FIG. 4, a data I/O bus allows for communications between the workstation monitor and a possible remote data acquisition system.

Figure 5:
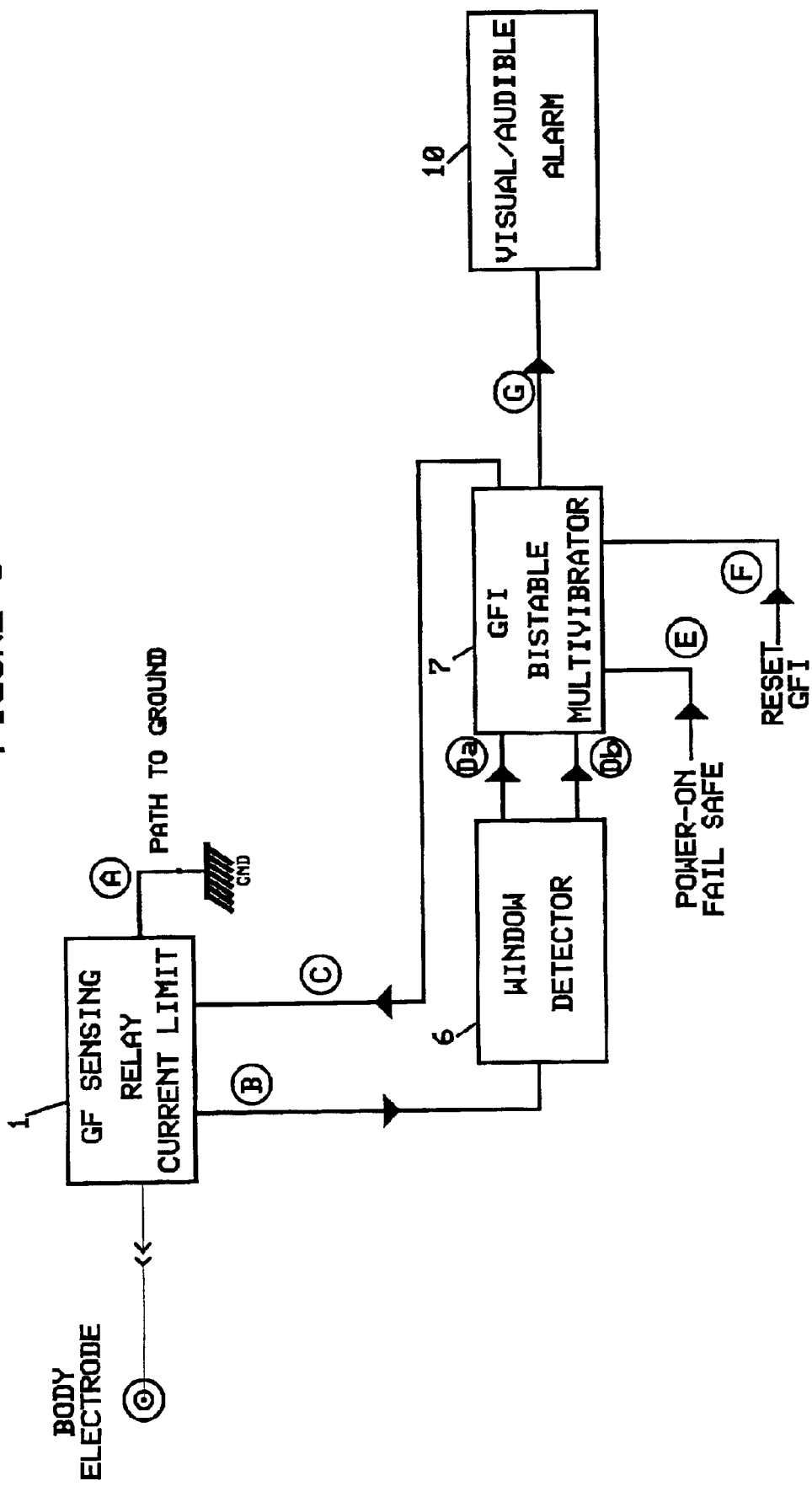
FIG. 5 depicts a block diagram of an implementation of the workstation monitor utilizing minimal component count.

FIG. 5 shows a block diagram of a "bare bones" implementation of a workstation monitor. Portions of this circuit are identical to the previous one, however, all stages not essential in establishing the path-to-ground and the ground fault sensing have been omitted. The triboelectric current enters the circuit at stage 1 (ground fault sensing/relay/current limiter) and is conducted into the ground (A).

Signal B is picked off at stage 1, and enters window detector 6. If the amplitude of signal B exceeds certain levels (such as in the case of an accidental touching of a live power wire), signals Da and Db will set the GFI bistable multivibrator stage 7 in a state such as to insure that the relay contact in stage 1 opens the path-to-ground (signal C). Input signal E (Power-on Fail Safe) to the GFI bistable multivibrator stage 7 insures that the relay is always in the open state when power is applied to the workstation monitor. The relay can be closed by manually resetting stage 7 with the reset GFI signal F. Output G from the GFI bistable multivibrator stage 7 will cause the audible/visual alarm means 10 to be activated.

Figure 6:
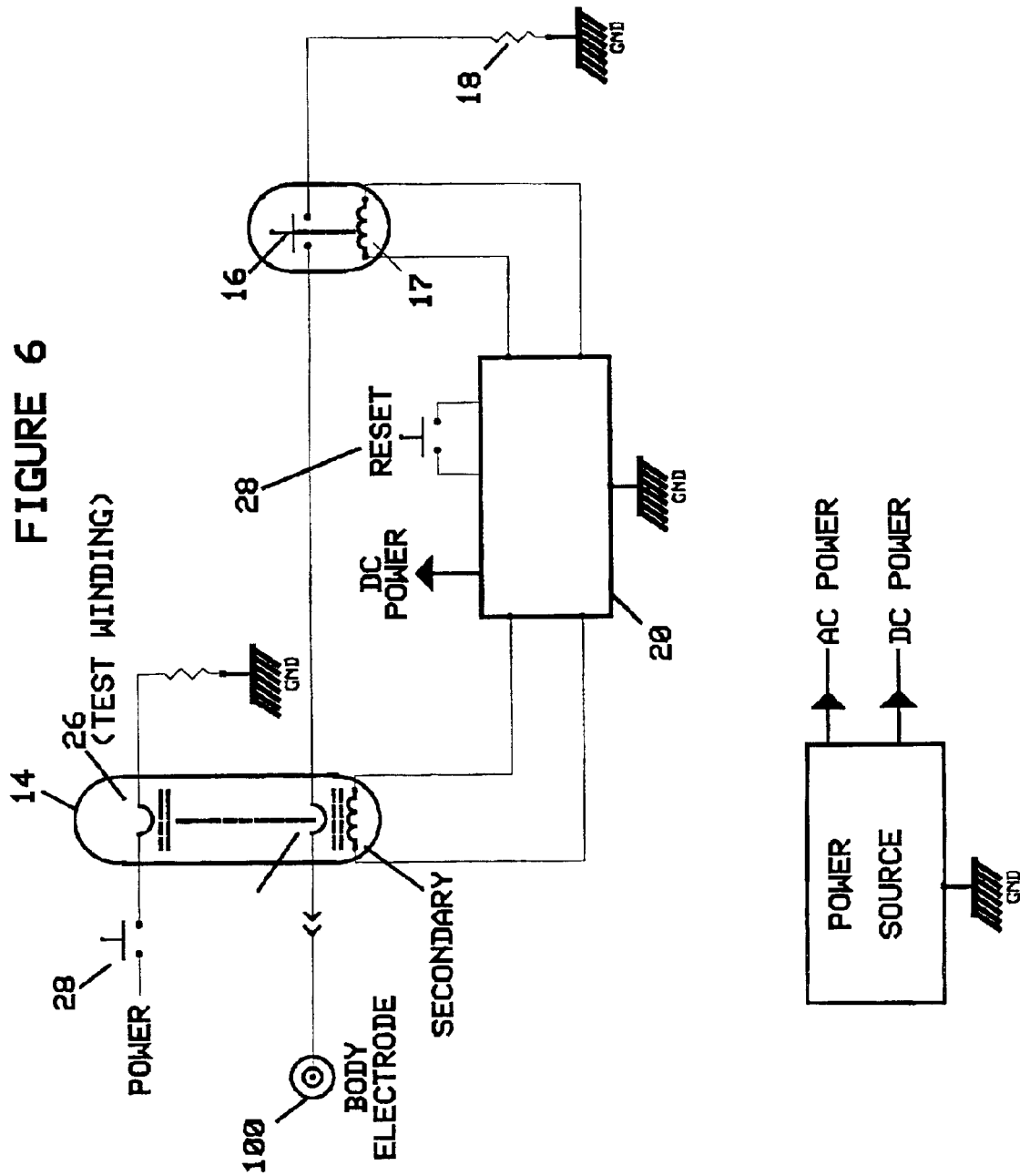
FIG. 6 shows a diagram of a further simplified workstation monitor.

An even further simplification of a "minimal" workstation monitor is illustrated in FIG. 6. This circuit is based on commercially available Ground Fault Interrupter Integrated Circuits such as the National Semiconductor LM1851. The triboelectric current is picked up by body electrode 100 and flows through a path comprising the primary of current transformer 14, relay contacts 16, and bleeder resistor 18. The value of this resistor added to the value of the skin-to-electrode resistance will largely determine the worst case body voltage potential excursion. (This assumes that all other resistors in the path are negligible with respect to the bleeder resistor 18 and the skin electrode.) The secondary of the current transformer 14 is connected to the input of ground fault interrupter integrated circuit 20. If an operator accidentally touches a 50 or 60 Hz live power distribution wire, a potentially dangerous current will flow through the path-to-ground. When the current exceeds a certain level, such as for example specified in Underwriter's Laboratories' publication UL 943, circuit 20 will cause relay contact 16 to open, thus interrupting the path-to-ground. The circuitry in IC 20 is executed such that contact 16 can only close when circuit 20 is properly powered, either from an AC power line derived power source, or from batteries.

The bistability of the relay action can be executed either electronically in IC 20 in conjunction with reset contact 22, or electromechanically in relay 17 with a suitable mechanical reset mechanism, or with a combination of the two. A further improvement to the monitor circuit is the addition of test winding 26 to the current transformer. Closure of contact 28 allows a test current to flow with amplitude such that a fault current is simulated. The test current is derived from the power source.

Additional Detection Means:

FIGS. 7–10 show additional arrangements and circuits which allow positive determination of whether a wrist strap is properly worn or not. FIGS. 7a–d depict possible arrangements of bracelet type body electrodes with a switch incorporated in the bracelet. FIG. 7a is a non-split bracelet 100 with a "normally open" switch 101. When the bracelet is not properly worn or insufficiently tight around the wrist, the contact will be open. FIG. 7b depicts a non-split bracelet 100 with a "normally closed" switch 101'. Similarly, FIGS. 7c and 7d respectively depict split bracelets 100' with a "normally open" switch 101 and a "normally closed" switch 101'.

Connectors 102 allow connection with the circuitry of the workstation monitor. The connectors 102 may or may not include electrical keying, mechanical keying, or a combination of both. Keying 103 is accomplished by assigning a certain value resistor for a given type of wrist strap. This allows the workstation monitor to recognize which body electrode is being used.

Certain detection schemes will allow sharing of a conductor, thus reducing the number of conductors required in the lead between the body electrode and the workstation monitor. In the circuit shown in FIG. 8, for example, the conductor connected to one of the switch poles is common with the path-to-ground conductor. Shown is a non-split body electrode 100 with a normally closed switch 101'. One of the poles of the switch 101' is electrically connected with the body electrode 100. A dual conductor lead with a suitable connecter 104 at the other side of switch 101' allows for connection to the workstation monitor circuitry, which is substantially identical to the circuit illustrated in detail in FIG. 3.

Two stages have been added for the detection scheme shown in FIG. 8 that allow the monitor to determine if a user is wearing the body electrode 100 properly, the stages being an oscillator circuit 30 and a bandpass filter/detector 32. An output signal from oscillator circuit 30, when normally closed switch 101 is in the closed position (the wrist strap is not worn properly), is provided as an input to the band pass filter/detector 32. This signal thus travels down the same path-to-ground conductor as the triboelectric current. After processing, an output signal A is generated by the band pass filter/detector 32 which signals the workstation monitor circuitry that switch 101' is closed, and activates an alarm in the workstation monitor circuit. This situation occurs only when the body electrode 100 is not being worn properly. When the body electrode 100 is properly worn, switch 101' will be open, and intended operation of the workstation monitor continues.

Figure 9:
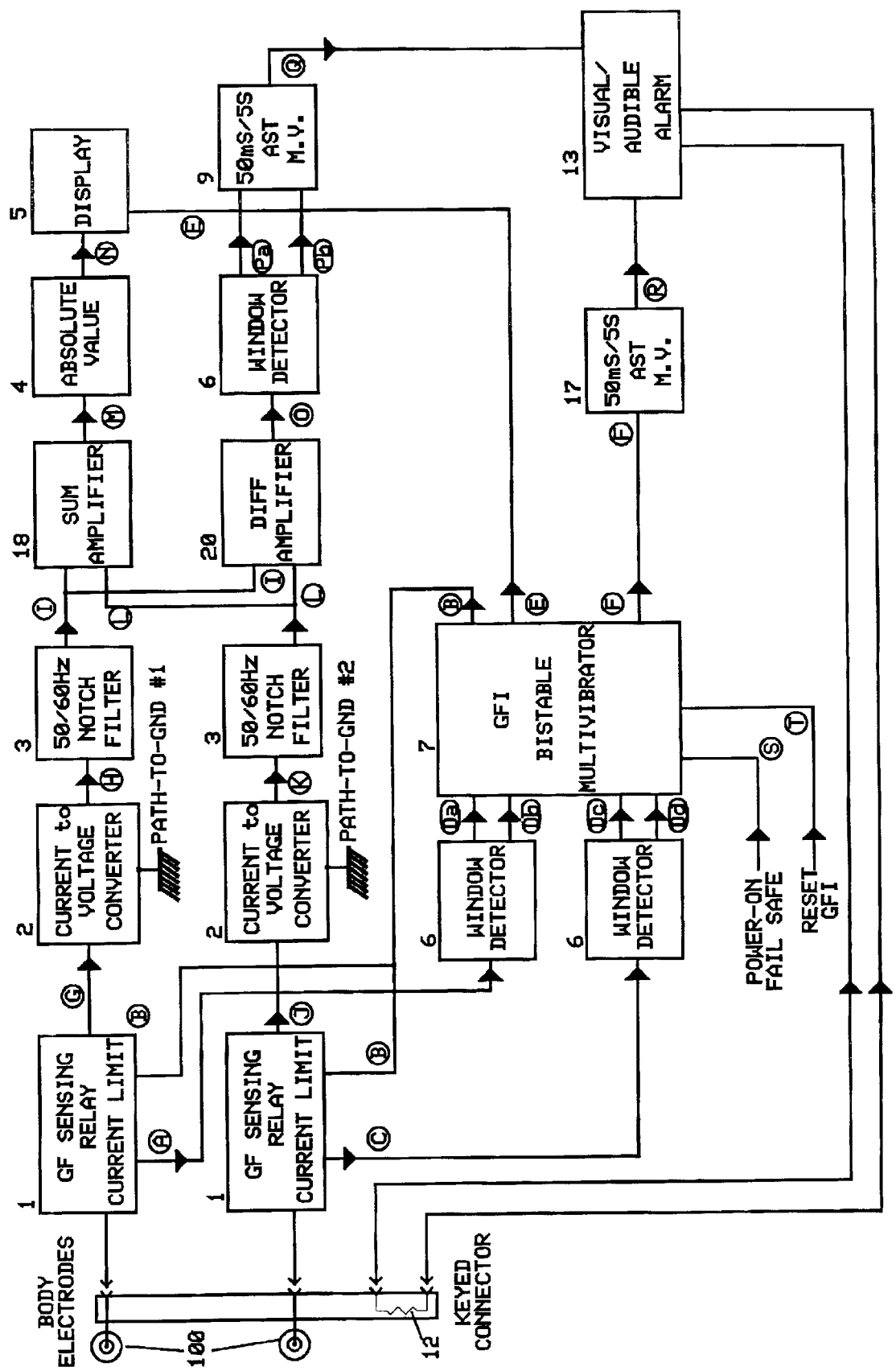
FIG. 9 is a block diagram for a redundant path-to-ground arrangement.

FIG. 9 shows the block diagram of a detection method based on a dual body electrode, for a redundant path-to-ground arrangement. Two body electrodes 100, which should be isolated from each other, are connected to identical signal shaping circuit stages which are substantially identical to those described in relation to FIG. 3, and which comprise a ground fault sensing/relay/current limit stage 1, a current-to-voltage converter 2, and a 50/60 Hz notch filter 3. Since the circuits in the two signal shaping paths are identical, and provided the contact resistances between the skin and the electrodes 100 are substantially the same, equal currents will flow through both paths-to-ground. Signals I and L will therefore be substantially identical. Signals I and L are further processed in parallel through a sum amplifier 18 and a difference amplifier 20. Output signal M, having passed through the sum amplifier 18, is therefore proportional to the sum of the fractional triboelectric currents flowing down the two paths-to-ground, and thus represents the total triboelectric current generated by the shoe sole/surface interaction. Signal M is then processed through an absolute value detector 4 and a display 5, similar to the process described relative to FIG. 3. Signal O at the output of difference amplifier 20 is proportional to the difference of the fractional triboelectric currents. As long as both paths-to-ground are substantially identical, signal O will be near zero. If, for whatever reason, one of the paths would be compromised, the amplitude of signal O will be different from zero. If the amplitude of signal O exceeds a set threshold level of window detector 6, the asymmetrical 50 mS/5S astable multivibrator 9 is triggered, thereby activating the visual/audible alarm 10, and thus announcing that one of the two paths-to-ground has been compromised, and that one of the body electrodes is no longer in proper contact with the operator's skin.

The detection of an accidental touch with a live power distribution wire is made redundant by using two window detector stages 6, each of them capable of triggering GFI bistable multivibrator 7. Both paths-to-ground have isolated-from-each-other relay contacts in their circuits. The relay contacts are located in the GFI sensing/relay/current limit stages, and interrupt the path to ground.

Figure 10:
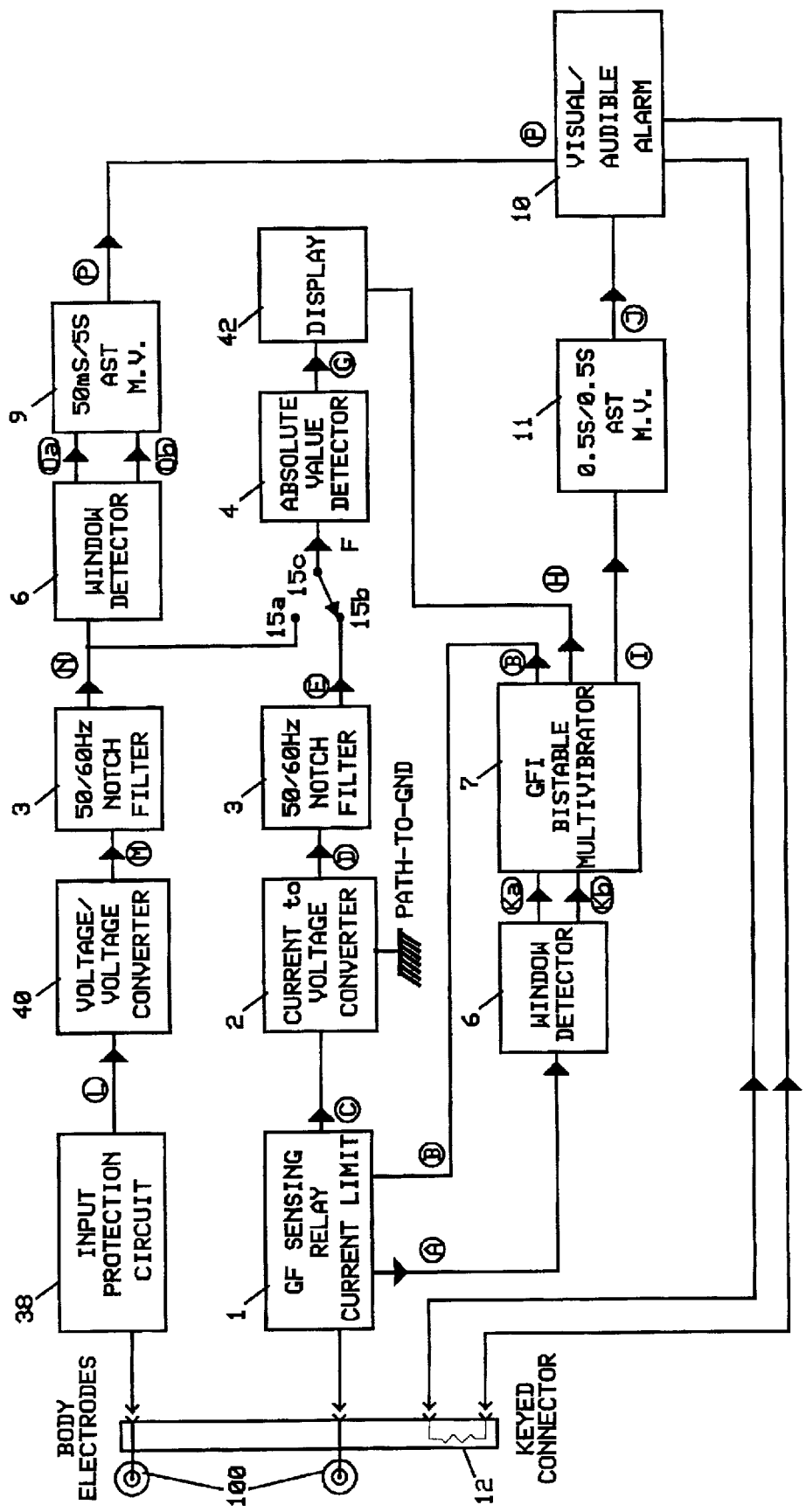
FIG. 10 shows an ESC Workstation arrangement based on two body electrodes.

FIG. 10 the block diagram of another workstation arrangement based on two body electrodes 100. In this arrangement, only a first body electrode 100 establishes the path-to-ground, whereas a second body electrode 100 is used to measure body voltage potential. The path-to-ground circuitry is substantially identical to those described above with reference to FIG. 3. The body voltage potential path includes an input protection circuit 38, followed by a voltage follower 40, which represents a very high input impedance to the body electrode 100. These stages are followed by a 50/60 Hz notch filter 3.

Signal N, proportional to the body voltage potential, goes to a window detector 6, and, if the amplitude of signal N exceeds certain preset values, signal Oa or Ob will trigger the astable multivibrator 9, which in turn, will set off the visual/audible alarm 10. The amplitude of signal N can only exceed the threshold levels of window detector 6 only when the triboelectric current path-to-ground is compromised.

Switch 44 allows either the triboelectric current or the body voltage potential to be displayed on a suitable display 42. An absolute value detector 4 may be included in the display circuitry if desired. It is also possible to eliminate selector switch 44 by adding a second display 42 so that both channels can be displayed simultaneously. The triboelectric current is then displayed on a first display 42, and the body voltage potential is shown on a second display 42. The absolute value detector 4 and display 42 are substantially identical to those described with reference to FIG. 3.

Because of the very high input impedance of the voltage channel, degradation of the skin-to-electrode resistance in the voltage channel does not come into play in the accuracy of the voltage measurement. The body voltage measurement is not compromised because the input impedance of the voltage amplifier chain is orders of magnitude higher than the skin-to-electrode resistance. The approach shown in FIG. 10 is thus well suited for use with existing split wrist straps with their inherently unreliable skin-to-electrode resistance. For example if the effect of a conduction improving gel between wrist and electrode wears off, thereby compromising the integrity of the path-to-ground, an operator's attention will be drawn by increasingly frequent alarms.

The above disclosure is not intended as limiting. Those skilled in the art will readily observe that numerous modifications and alterations of the device may be made while retaining the teachings of the invention. Accordingly, the above disclosure should be construed as limited only by the restrictions of the appended claims.

What is claimed is:

1. A circuit to control and monitor voltage potential on a human body comprising:

an electrode in contact with skin of an operator, a ground fault sensing/relay/current limit stage, and a current-to-voltage converter in a path-to-ground, a filter, an absolute value amplifier, display means, a window detector, a ground fault bistable multivibrator, an astable multivibrator, an activity detector means, and an alarm means; wherein triboelectric current bursts detected by said electrode enter said ground fault sensing/relay/current limit stage, a signal from said ground fault sensing/relay/current limit stage being processed through said current-to-voltage converter, said filter, and said absolute value amplifier, said absolute value amplifier converting bipolar signals into positive unipolar signals, said unipolar signals driving said display means; and wherein a first signal is picked off from said display means to drive said activity detector means, and concurrently, a second signal is picked off from said ground fault sensing/relay/current limit stage, said second signal being processed through said window detector and through said ground fault bistable multivibrator, outputs of said activity detector means and said ground fault bistable multivibrator drive multivibrators which in turn drive said alarm means; such that said alarm means is activated when said circuit does not detect said triboelectric current bursts and when inadvertent contact with a power source occurs.

2. The circuit as claimed in claim 1 wherein:

an output signal of said ground fault bistable multivibrator causes a relay to open if the operator accidentally contacts a live power wire.

3. The circuit as claimed in claim 1 wherein:

an output signal of said ground fault bistable multivibrator ensures blanking of said display means unless said ground fault bistable multivibrator has been manually reset.

4. The circuit as claimed in claim 1 wherein:

a power-on fail safe means insures that said ground fault bistable multivibrator is set to a proper logical state after any interruption in power supply.

5. The circuit as claimed in claim 1 wherein:

functions of said absolute value amplifier, said ground fault bistable multivibrator, said astable multivibrator, and said activity detector means are executed by a microprocessor.

6. The circuit as claimed in claim 1 wherein:

said circuit comprises two electrodes in contact with the skin of the operator, said two electrodes being electrically isolated, and each of said two electrodes being an element of an independent path-to-ground; wherein said alarm means is activated if a difference between a current flowing through a first one of said paths-to-ground and a current flowing through a second one of said paths-to-ground is greater than a predetermined level, said difference indicating a compromise in at least one of said paths-to-ground.

7. The circuit as claimed in claim 1 wherein:

said circuit comprises two electrodes in contact with the skin of the operator, said two electrodes being electrically isolated, and each of said two electrodes being an element of an independent path-to-ground; wherein said alarm means is activated if a voltage potential detected in either of said paths-to-ground is greater than a predetermined level, said voltage potential indicating a compromise in at least one of said paths-to-ground.

* * * * *